United States Patent [19]

Nakajima

[11] Patent Number: 4,552,849
[45] Date of Patent: Nov. 12, 1985

[54] METHOD FOR DETERMINATION OF FORMALDEHYDE

[75] Inventor: Motoo Nakajima, Noda, Japan

[73] Assignee: Kikkoman Corporation, Japan

[21] Appl. No.: 632,000

[22] Filed: Jul. 18, 1984

[30] Foreign Application Priority Data

Jul. 26, 1983 [JP] Japan .................. 58-135168

[51] Int. Cl.$^4$ .................. G01N 21/64; G01N 21/77
[52] U.S. Cl. .................................. 436/130; 436/172
[58] Field of Search .................. 436/128, 130, 172

[56] References Cited

U.S. PATENT DOCUMENTS 4,438,206 3/1984 Nakajima .................. 436/130

FOREIGN PATENT DOCUMENTS 13034 4/1976 Japan .................. 436/128

OTHER PUBLICATIONS

Sidney Belman, "The Fluorimetric Determination of Formaldehyde", Anal. Chim. Acta. 29, pp. 120–126, (1963).

Bartos et al., "Colorimetric and Fluorimetric Determination of Aldehydes and Ketones" *Pure & Appl. Chem.*, (GB), vol. 51, No. 8, Aug. 1979.

Slawinska et al., "Chemiluminescent Flow Method for Determination of Formaldehyde" *Anal. Chem.*, vol. 47, No. 13, Nov. 1975.

*Primary Examiner*—William F. Smith
*Assistant Examiner*—K. M. Hastings
*Attorney, Agent, or Firm*—Banner, Birch, McKie & Beckett

[57] ABSTRACT

In a method of formaldehyde determination by measuring the fluorescence of a fluorescent substance formed by the reaction of a formaldehyde-containing solution with a fluorescent reagent capable of forming said fluorescent substance by the reaction with formaldehyde, the improvement which comprises using as said fluorescence reagent a compound represented by the general formula $CH_3C(NH_2)=CHCO_2R$, wherein R represents an alkyl group having 1 to 4 carbon atoms.

4 Claims, 3 Drawing Figures

METHOD FOR DETERMINATION OF FORMALDEHYDE

BACKGROUND OF THE INVENTION

1. Field of the Invention

This invention relates to a novel method for determination of formaldehyde.

2. Description of the Prior Art

Since formaldehyde is produced as a reaction product during the course of several enzymatic reactions, the determination of formaldehyde has been carried out for assaying the enzymatic activities in said reactions or the substrate concentrations before the occurrence of enzymatic reactions.

For example, in the determination of triglycerides in plasma or tissues, the triglycerides are saponified to give glycerol, the glycerol formed is oxidized to give formaldehyde, the quantity of which is then determined; or in the determination of creatinine in serum or urine by an enzymatic method, the quantity of the creatinine is obtained by determination of formaldehyde resulting from the enzymatic reaction.

Formaldehyde is used as a raw material in the production of various resins. It is used also in improving the strength of textile fibers or improving the fiber strength in paper making. In addition, it is used as a fungicide or antiseptic. Further, it has been known that there are some of the daily necessaries such as tablewares, plywood furnitures and clothing articles which liberate a small amount of formaldehyde either in vapor state or as dissolved in water. The liberated formaldehyde is harmful to the human body, causing sometimes a poisoning which may lead to a rash.

For the above reasons, the determination of formaldehyde is important in the above-noted industrial fields as well as from the standpoint of hygienic chemistry.

For the determination of formaldehyde, there have heretofore been known several methods including, besides various colorimetric methods of determination, a method in which formaldehyde is allowed to react with an acetylacetone reagent in the presence of an ammonium salt and the resulting diacetyldihydrolutidine is fluorimetrically determined [S. Belman, Anal. Chim. Acta, Vol. 29, pp. 120–6 (1963)]. But, this method is unsuitable for the determination of an extremely small amount of formaldehyde because of the insufficient detection sensitivity due to the low fluorescence intensity of the formed fluorescent substance. The method has also a disadvantage in that the reaction between formaldehyde and acetylacetone is slow (requiring 5 hours at 20° C.) and, when the reaction temperature is elevated for shortening the reaction time, the coloration of reaction mixture takes place, affecting adversely the accuracy of the determination.

The present inventors have previously been granted a patent for an improved method for determination of formaldehyde (U.S. Pat. No. 4,438,206) which comprises, in a method of formaldehyde determination by measuring the fluorescence of a fluorescent substance formed by allowing a formaldehyde-containing solution to react with an acetylacetone reagent, measuring the fluorescence in the presence of a serum albumin, particularly a bovine serum albumin.

Although this method has a high detection sensitivity and permits detecting an extremely small amount of formaldehyde with good sensitivity, it has not solved the problem of long reaction time and further has newly brought about an operational problem of requiring the addition of a substance other than the fluorescence reagent, namely a serum albumin.

Under the circumstances, the present inventors made an extensive study to find a more satisfactory method for determination of formaldehyde. As a result, it was found that the determination of formaldehyde can be performed with good accuracy and high speed when a compound represented by the general formula $CH_3C(NH_2)=CHCO_2R$, wherein R represents an alkyl group having 1 to 4 carbon atoms, is used as a fluorescence reagent capable of forming a fluorescent substance by the reaction with formaldehyde. Based on this finding, this invention has been accomplished.

SUMMARY OF THE INVENTION

An object of this invention is to provide a highly sensitive method for determination of formaldehyde with high speed.

Other objects and advantages of this invention will become apparent from the descriptions below.

BRIEF DESCRIPTION OF THE DRAWINGS

In the accompanying drawings.

DETAILED DESCRIPTION OF THE INVENTION

Figure 1:
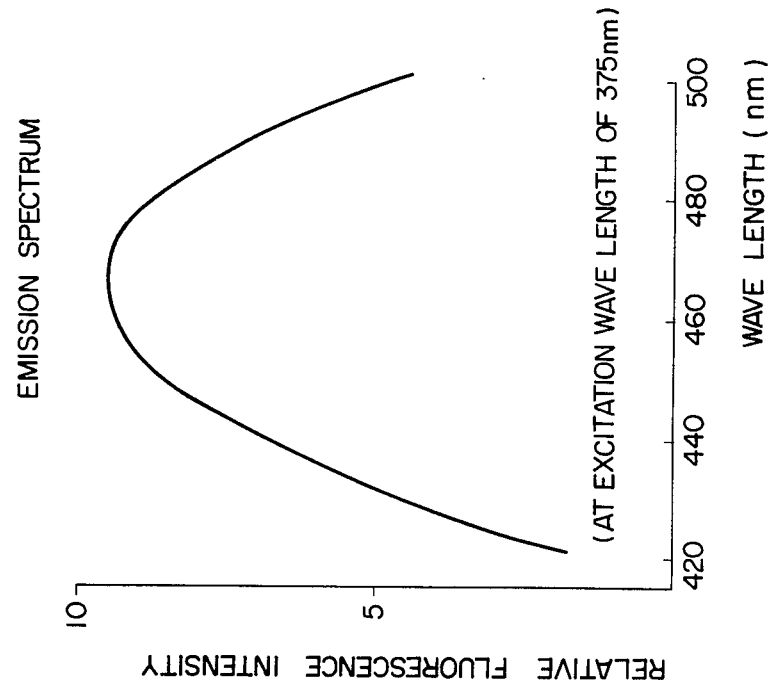
FIGS. 1 and 2 show the excitation spectrum and the emission spectrum, respectively, of the fluorescent substance formed by the reaction of a standard solution of formaldehyde with methyl 3-aminocrotonate, a fluorescence reagent.

According to this invention, there is provided, in a method of formaldehyde determination by measuring the fluorescence of a fluorescent substance formed by the reaction of a formaldehyde-containing solution with a fluorescence reagent capable of forming said fluorescent substance by the reaction with formaldehyde, the improvement which comprises using as said fluorescence reagent a compound represented by the general formula $CH_3C(NH_2)=CHCO_2R$, wherein R represents alkyl group having 1 to 4 carbon atoms.

This invention will be further described in detail below.

(1) Preparation of fluorescence reagents

A compound represented by the general formula $CH_3C(NH_2)=CHCO_2R$, wherein R represents an alkyl group having 1 to 4 carbon atoms, such as methyl 3-aminocrotonate (R in the above general formula being a methyl group) or ethyl 3-aminocrotonate (R in the above formula being an ethyl group), is dissolved in an organic solvent to form a solution containing said compound in a molarity of 0.01 to 2.

The organic solvents for use in the present method include, for example, methanol, ethanol, propanol, isopropanol, ethyleneglycol dimethyl ether, ethyleneglycol monomethyl ether, triethylene glycol, dioxane, acetone, pyridine, acetonitrile, dimethylsulfoxide and dimethylformamide.

(2) Reaction and determination

A sample solution containing formaldehyde is mixed with an approximately equal amount of a phosphate or ammonium acetate buffer solution which has been adjusted to a concentration of 0.01 to 3, preferably 0.05 to 0.2, in molarity and a pH of 4 to 8, preferably 5.0 to 6.5. To the mixture was then added 1 to 50% of the fluorescence reagent prepared above, and the resulting mixture was allowed to react at 20° to 80° C. for 1 to 60 minutes.

The reaction time can be shortened by elevating the reaction temperature; for example, it is about 60 minutes at 20° C. and about 15 minutes at 37° C.

The above reaction results in the formation of a fluorescent substance in the reaction mixture. It is irradiated with a light having an excitation wave length specific to said fluorescent substance (for example 320 to 400 nm, particularly 370 to 380 nm); the fluorescence of the reaction mixture is measured at characteristic emission wave length (for example 430 to 500 nm, particularly 460 to 470 nm); and the formaldehyde content is determined by using the calibration curve separately obtained.

The above-mentioned method for determination of formaldehyde according to this invention enables the determination of formaldehyde with markedly improved accuracy and with short reaction time as compared with previously known fluorimetric determination of formaldehyde.

The effect of the method of this invention will be illustrated below with reference to an Experimental Example.

Experimental Example (1) Preparation of standard formaldehyde solution

Formaldehyde was dissolved in distilled water to form solutions containing respectively 10.67, 21.34, 53.36, 80.04 and 106.70 nanograms (ng) of formaldehyde in 2 ml.

(2) Preparation of fluorescence reagents (a) Preparation of methyl 3-aminocrotonate [$CH_3C(NH_2)=CHCO_2CH_3$] reagent Methyl 3-aminocrotonate (manufactured by Aldrich Co.) was recrystallized from ethyl ether; 2.3 g of the recrystallized product was dissolved in dimethylformamide to give a total volume of 100 ml.

(b) Preparation of ethyl 3-aminocrotonate [$CH_3C(NH_2)=CHCO_2C_2H_5$] reagent

Ethyl 3-aminocrotonate (manufactured by Aldrich Co.) (2.5 ml) was dissolved in dimethyl sulfoxide to give a total volume of 100 ml.

(c) Preparation of acetylacetone reagent

A 2 M ammonium acetate buffer solution (adjusted to pH 6.0 with acetic acid) was mixed with 0.2 ml of acetylacetone, stirred to form a solution, and then made up with the same buffer solution to 100 ml.

(3) Fluorimetric determination of formaldehyde (a) Method of this invention

Each 2 ml of the standard formaldehyde solutions of different concentrations prepared in (1) above was mixed with 2 ml of 0.1 molar phosphate buffer solution (pH 5.5) and the mixture was then admixed with 200 μl of either methyl 3-aminocrotonate reagent prepared in (2) (a) or ethyl 3-aminocrotonate reagent prepared in (2) (b). After thorough stirring, the mixture was allowed to react at 37° C. for 15 minutes, and the fluorescence intensity was determined at fluorescence excitation and emission wave lengths of 375 and 465 nm, respectively.

Figure 2:
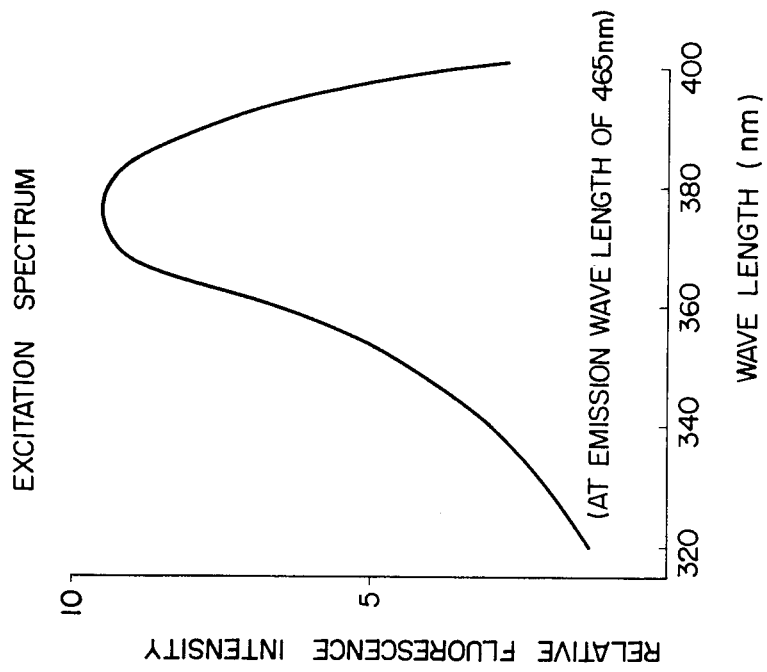

The excitation spectrum (at emission wave length of 465 nm) and the emission spectrum (at excitation wave length of 375 nm) of the fluorescent substance formed by the reaction with methyl 3-aminocrotonate were as shown in FIGS. 1 and 2, respectively.

(b) Control method

Each 2 ml of the standard formaldehyde solution of different concentrations prepared in (1) above was mixed with 2 ml of the acetylacetone reagent prepared in (2) (c). After thorough stirring, the mixture was allowed to react at 37° C. for 60 minutes, and the fluorescence intensity was determined at fluorescence excitation and emission wavelengths of 415 and 510 nm, respectively.

The fluorimetric determination was performed in all cases under the following conditions:

Spectrofluorimeter: Type FP 550 of Nihon Bunko K.K.

Excitation wave length: slit 10 mm.

Emission wave length: slit 20 nm; selector=10; sensitivity=10; variable 8.

The blank value was obtained in the same manner as described above, except that 2 ml of distilled water was used in place of 2 ml of the standard formaldehyde solution.

Figure 3:
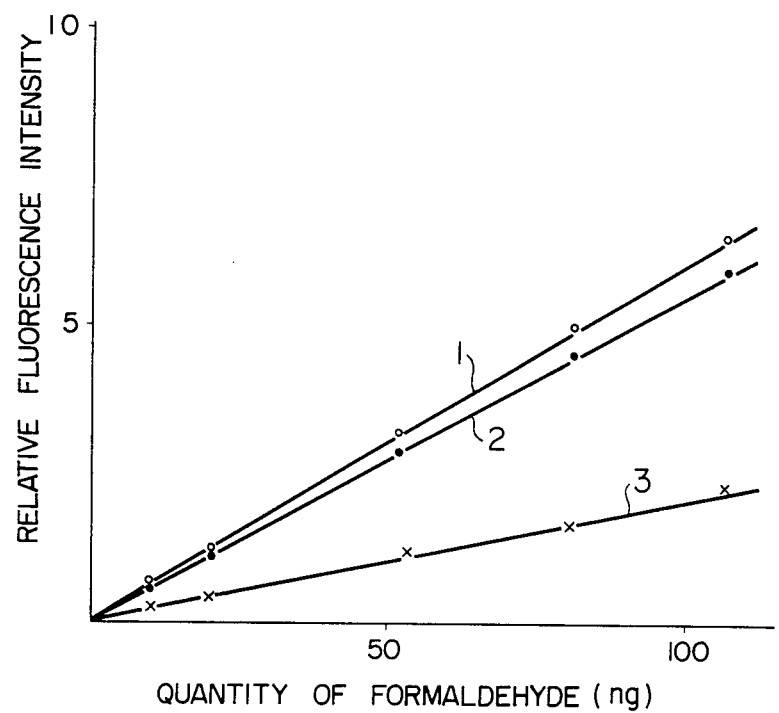
FIG. 3 is a graph (standard calibration curves) representing the relationship between the amount of formaldehyde and the relative fluorescence intensity; line (1) (indicated by —o—o—) is obtained by using methyl 3-aminocrotonate as the fluorescence reagent, line (2) (indicated by —•—•—) by using ethyl 3-aminocrotonate and line (3) (indicated by —x—x—) by using acetylacetone.

The relationship between the quantity of formaldehyde and the relative fluorescence intensity (obtained by subtracting the blank value from the observed relative fluorescence intensity) was as shown in FIG. 3.

As is apparent from FIG. 3, the method of this invention gives about 3 times as high a relative fluorescence intensity as that obtained by the control method and consequently enables a more accurate determination of formaldehyde.

This invention will be illustrated further with reference to an Example.

EXAMPLE

To 2 ml of a sample solution containing an extremely small amount of formaldehyde, were added 200 μl of the methyl 3-aminocrotonate reagent as described in (2) (a) of Experimental Example as well as 2 ml of a 0.1 molar phosphate buffer solution (pH 5.5). After thorough stirring, the mixture was allowed to react at 37° C. for 15 minutes. The resulting reaction mixture was subjected to the fluorimetric determination at fluorescence excitation and emission wave lengths of 375 and 465 nm, respectively. The blank value was obtained in the same manner as described above, except that 2 ml of distilled water was used in place of 2 ml of the formaldehyde-containing sample solution.

After subtraction of the blank value, the relative fluorescence intensity was 2.34. From this value, the quantity of formaldehyde was determined by means of the graph shown in FIG. 3 (standard calibration curve). The formaldehyde content was found to be 40.0 ng in 2 ml of the sample.

What is claimed is:

1. In a method of formaldehyde determination by measuring the fluorescence of a fluorescent substance formed by the reaction of a formaldehyde-containing solution with a fluorescence reagent capable of forming said fluorescent substance by the reaction with formaldehyde, the improvement which comprises using as said fluorescence reagent a compound represented by the general formula $CH_3C(NH_2)=CHCO_2R$, wherein R represents an alkyl group having 1 to 4 carbon atoms.

2. A method according to claim 1, wherein a compound of said general formula wherein R is a methyl group is used.

3. A method according to claim 1, wherein a compound of said general formula wherein R is an ethyl group is used.

4. A method of formaldehyde determination which comprises mixing a formaldehyde-containing sample solution with an equal amount of a phosphate or ammonium acetate buffer solution which has been adjusted to a concentration of 0.01 to 3 in molarity and a pH of 4 to 8, adding to the mixture 1 to 50% of a 0.01 to 2 molar solution of methyl 3-aminocrotonate, $CH_3C(NH_2)=CHCO_2CH_3$, or ethyl 3-aminocrotonate, $CH_3C(NH_2)=CHCO_2C_2H_5$, in an organic solvent, allowing the resulting mixture to react at 20 to 80° C. for 1 to 60 minutes, and then determining the fluorescence of the resulting fluorescent substance.

* * * * *